(12) United States Patent
Vermeiren et al.

(10) Patent No.: US 8,518,370 B2
(45) Date of Patent: Aug. 27, 2013

(54) METALLOALUMINOPHOSPHATE MOLECULAR SIEVES WITH LAMELLAR CRYSTAL MORPHOLOGY AND THEIR PREPARATION

(75) Inventors: Walter Vermeiren, Houthalen (BE); Nikolai Nesterenko, Nivelles (BE); Carolina Petitto, Montpellier (FR); Francesco Di Renzo, Montpellier (FR); Francois Fajula, Teyran (FR)

(73) Assignees: Total Petrochemicals Research Feluy, Seneffe (Feluy) (BE); Centre National de la Recherche Scientifique (CNRS), Paris (FR)

( * ) Notice: Subject to any disclaimer, the term of this patent is extended or adjusted under 35 U.S.C. 154(b) by 826 days.

(21) Appl. No.: 12/530,860

(22) PCT Filed: Mar. 10, 2008

(86) PCT No.: PCT/EP2008/052807
§ 371 (c)(1),
(2), (4) Date: Mar. 24, 2010

(87) PCT Pub. No.: WO2008/110526
PCT Pub. Date: Sep. 18, 2008

(65) Prior Publication Data
US 2010/0179296 A1     Jul. 15, 2010

Related U.S. Application Data

(60) Provisional application No. 60/939,440, filed on May 22, 2007.

(30) Foreign Application Priority Data

Mar. 13, 2007   (EP) .................................... 07300860

(51) Int. Cl.
C07C 1/20      (2006.01)
B01J 29/85     (2006.01)
C01B 39/54     (2006.01)
C01B 37/08     (2006.01)
B01J 29/00     (2006.01)
B01J 35/02     (2006.01)
B01J 29/06     (2006.01)

(52) U.S. Cl.
CPC ................ B01J 29/85 (2013.01); B01J 29/005 (2013.01); B01J 35/026 (2013.01); *B01J 2029/062* (2013.01); C07C 1/20 (2013.01); *C07C 2529/85* (2013.01); C01B 39/54 (2013.01); C01B 37/08 (2013.01)
USPC ............. 423/701; 423/707; 423/305; 502/60; 585/640

(58) Field of Classification Search
USPC ............ 423/701, 707, 305; 502/60; 585/640
See application file for complete search history.

(56) References Cited

U.S. PATENT DOCUMENTS

| | | | |
|---|---|---|---|
| 4,677,243 A | 6/1987 | Kaiser | |
| 6,953,767 B2 * | 10/2005 | Janssen et al. | ................ 502/214 |
| 2005/0090390 A1 | 4/2005 | Venkatathri et al. | |
| 2006/0147364 A1 | 7/2006 | Venkatathri et al. | |

FOREIGN PATENT DOCUMENTS

WO         02070407 A      9/2002

OTHER PUBLICATIONS

Wu X et al, "Effect of Feed Composition on Methanol Conversion to Light Olefins over SAPO-34", Applied Catalysis A: General, Elsevier Science, Amsterdam, NL, vol. 218, No. 1-2, Sep. 25, 2001, pp. 241-250, XP004300335, ISSN: 0926-860X, pp. 244-245.

* cited by examiner

*Primary Examiner* — David M Brunsman (57) ABSTRACT

The present invention relates to metalloaluminophosphate (MeAPO) molecular sieve with lamellar crystal morphology having an empirical chemical composition on an anhydrous basis, after synthesis and calcination, expressed by the formula $H_xMe_yAl_zP_kO_2$ wherein, $y+z+k=1$ $x<=y$ said molecular sieve having predominantly a plate crystal morphology in which the width (W) and the thickness (T) are W/T is >=10 The above metalloaluminophosphate (MeAPO) molecular sieve can be made by a method which comprises: a) forming a reaction mixture containing a texture influencing agent (TIA), an organic templating agent (TEMP), at least a reactive inorganic source of $MeO_2$ insoluble in the TIA, reactive sources of $Al_2O_3$ and $P_2O_5$, b) crystallizing the above reaction mixture thus formed until crystals of the metalloaluminophosphate are formed, c) recovering a solid reaction product, d) washing it with water to remove the TIA and e) calcinating it to remove the organic template. The present invention also relates to catalysts consisting of the above MeAPO molecular and relates to a process for making an olefin product from an oxygen-containing, halogenide-containing or sulphur-containing feedstock.

23 Claims, 9 Drawing Sheets fig 1A fig 1B fig 2 fig 3A fig 3B fig 4 fig 5A fig 5B fig 6A fig 6B fig 6C

Fig 6D fig 7 fig 8

METALLOALUMINOPHOSPHATE MOLECULAR SIEVES WITH LAMELLAR CRYSTAL MORPHOLOGY AND THEIR PREPARATION

This is a 371 filing of PCT/EP2008/052807, filed Mar. 10, 2008.

FIELD OF THE INVENTION

The present invention relates to metalloaluminophosphate (MeAPO) molecular sieves with lamellar crystal morphology and their preparation. The metalloaluminophosphate molecular sieves of the invention are useful as catalysts in a variety of processes including cracking, hydrocracking, isomerization, reforming, dewaxing, alkylation, transalkylation, conversion of methanol to light olefins. The limited supply and increasing cost of crude oil has prompted the search for alternative processes for producing hydrocarbon products. One such process is the conversion of oxygen-containing, halogenide-containing or sulphur-containing organic compounds to hydrocarbons and especially light olefins (by light olefins is meant $C_2$ to $C_4$ olefins) or gasoline and aromatics. The interest in the methanol to olefin (MTO) process is based on the fact that oxygenates, especially methanol can be obtained from coal, biomass, organic waste or natural gas by the production of synthesis gas which is then processed to produce methanol.

BACKGROUND OF THE INVENTION

U.S. Pat. No. 4,440,871 describes microporous crystalline silicoaluminophosphates (referred as SAPO) the pores of which are uniform and have nominal diameters of greater than about 3 Angstroms and whose essential empirical chemical composition in the as-synthesized and anhydrous form is $mR:(Si_xAl_yP_z)O_2$ wherein "R" represents at least one organic templating agent present in the intracrystalline pore system; "m" has a value of from 0.02 to 0.3; "m" represents the moles of "R" present per mole of $(Si_xAl_yP_z)O_2$; "x", "y" and "z" represent the mole fractions of silicon, aluminum and phosphorus respectively, present as tetrahedral oxides, said mole fractions being such that they are within a specific area in the ternary diagram $Si_xAl_yP_z$. Process for preparing said SAPO comprises forming a reaction mixture containing reactive sources of $SiO_2$, $Al_2O_3$, and $P_2O_5$ and an organic templating agent, said reaction mixture having a composition expressed in terms of molar oxide ratios of: $aR_2O:(Si_xAl_yP_z)O_2:bH_2O$ wherein "R" is an organic templating agent; "a" has a value large enough to constitute an effective amount of "R" and is within the range of greater than 0 to 3; "b" has a value of from zero to 500; "x", "y" and "z" represent the mole fractions, respectively, of silicon, aluminum and phosphorus in the $(Si_xAl_yP_z)O_2$ constituent and each has a value of at least 0.01 and crystallizing the reaction mixture thus formed at a temperature of at least 100° C. until crystals of the silicoaluminophosphate are formed.

U.S. Pat. No. 6,207,872 relates to a process for converting methanol to light olefins comprising contacting the methanol with a catalyst at conversion conditions, the catalyst comprising a crystalline metallo aluminophosphate molecular sieve having a chemical composition on an anhydrous basis expressed by an empirical formula of: $(EL_xAl_yP_z)O_2$ where EL is a metal selected from the group consisting of silicon, magnesium, zinc, iron, cobalt, nickel, manganese, chromium and mixtures thereof, "x" is the mole fraction of EL and has a value of at least 0.005, "y" is the mole fraction of Al and has a value of at least 0.01, "z" is the mole fraction of P and has a value of at least 0.01 and x+y+z=1, the molecular sieve characterized in that it has predominantly a plate crystal morphology, wherein the average smallest crystal dimension is at least 0.1 micron and has an aspect ratio of less than or equal to 5.

U.S. Pat. No. 6,334,994 relates to a microporous crystalline silico-alumino-phosphate composition, the theoretical composition of which, on a water-free basis after synthesis and calcination, is: $H_wSi_xAl_yP_zO_2$ where w and x have a value between 0.01 and 0.05 and y and z are values between 0.4 and 0.6, wherein the composition is a mixed phase product comprising silico-alumino-phosphates of AEI and CHA structure prepared in one batch crystallization, not including mere physical mixtures, the product after calcination in air at 550° C. for 4 hours, produces a specific X-ray diffractogram and XRD-profiles.

EP 893159 relates to a method for preparing catalysts comprising silica-modified crystalline silicoaluminophosphate molecular sieves, which comprises adding an aluminum alkoxide to an aqueous amine or organic ammonium salt solution cooled at a temperature of not higher than 20° C., followed by hydrolysis, until a uniform aqueous aluminum hydroxide colloid or solution is formed, adding, to the colloid or solution, silica or other Si-source compounds, and phosphoric acid or other P-source compounds, if desired, along with a metal source selected from the group of Li, Ti, Zr, V, Cr, Mn, Fe, Co, Zn, Be, Mg, Ca, B, Ga and Ge, hydrothermally treating the resulting mixture to prepare a crystalline silicoaluminophosphate molecular sieve, and then modifying the crystalline silicoaluminophosphate molecular sieve with silica.

US 2005 0096214 (U.S. Pat. No. 6,953,767) relates to a process for making an olefin product from an oxygenate feedstock comprising contacting said oxygenate feedstock with a catalyst comprising a silicoaluminophosphate molecular sieve comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve, under conditions effective to form an olefin product.

It also describes a method for preparing the molecular sieve of said process that comprises (a) combining a reactive source of silicon, a reactive source of phosphorus and a hydrated aluminum oxide in the presence of an organic structure directing agent (template) to form a mixture;

(b) mixing and heating continuously the mixture prepared at step a) up to the crystallization temperature;

(c) maintaining the mixture at the crystallization temperature and under stirring for a period of time of from 2 to 150 hours;

(d) recovering crystals of the silicoaluminophosphate molecular sieve (e) wherein the mixture prepared at step a) has a molar composition within the following ranges:
$P_2O_5:Al_2O_3$ from 0.6:1 to 1.2:1
$SiO_2:Al_2O_3$ from 0.005:1 to 0.35:1
$H_2O:Al_2O_3$ from 10:1 to 40:1
and the template is a tetraethylammonium compound.

All these prior arts concern MeAPO with lamellar cubic or plate crystal morphology. In all the above prior arts only template and/or specific reaction conditions are used to influence the crystal structure of the material. It has been discovered that preparing said MeAPO in the presence of one template, one texture influencing agent, inorganic metal source, Al and P source, all these ingredients being in specific proportions, MeAPO with very thin lamellar plate crystal morphology are obtained. The template can be tetraethylammonium hydroxide (TEAOH) or an amine. The texture influencing agent can be an alcohol, a diol or glycerol.

U.S. Pat. No. 6,540,970 relates to a method for making a metalloaluminophosphate (MeAPO) molecular sieve, said process comprising the steps of:

providing a source of alumina, a source of phosphorus, water, and a template suitable for forming a MeAPO molecular sieve;

providing a source of metal including metal particles, said metal particles measuring, in their largest dimension, equal to or less than five nanometers;

providing a water soluble organic solvent capable of solubilizing said source of metal;

forming a synthesis mixture from said source of alumina, said source of phosphorus, said water, said template, said source of metal, and said solvent;

and forming a MeAPO molecular sieve from said synthesis mixture. Desirably, the water soluble organic solvent capable of solubilizing the source of the metal is selected from the group consisting of sulfoxides and $C_1$ to $C_5$ oxygenated hydrocarbons. Desirably, the oxygenated hydrocarbon is selected from the group consisting of alcohols (branched or normal), ketones, aldehydes, diols and acids. Useful solvents include one or more solvents selected from the group consisting of acetone, 1,2-propanediol, 1,3-propanediol, methanol, ethanol, propanol, isopropanol, butanol, and ethylene glycol. Desirably, the solvent is an alcohol. The products obtained are isocrystalline spheroidal particles comprising a SAPO molecular sieve. The particle measures from 0.5 microns to 30 microns in diameter.

This process doesn't lead to MeAPO with very thin lamellar plate crystal morphology.

BRIEF SUMMARY OF THE INVENTION

The present invention relates to metalloaluminophosphate (MeAPO) molecular sieve with lamellar crystal morphology having an empirical chemical composition on an anhydrous basis, after synthesis and calcination, expressed by the formula $H_xMe_yAl_zP_kO_2$ wherein, y+z+k=1 x<=y y has a value ranging from 0.0008 to 0.4 and advantageously from 0.005 to 0.18 z has a value ranging from 0.25 to 0.67 and advantageously from 0.38 to 0.55 k has a value ranging from 0.2 to 0.67 and advantageously from 0.36 to 0.54 said molecular sieve having predominantly a plate crystal morphology in which the width (W) and the thickness (T) are such as:

W/T is >=10 and advantageously ranges from 10 to 100.

In a preferred embodiment T is <=0.15 μm, more desirably <=0.10 μm, more desirably <=0.08 μm, advantageously ranges from 0.01 to 0.07 μm and preferably from 0.04 to 0.07 μm.

In an advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

In an advantageous embodiment the MeAPO of the invention have essentially a structure CHA or AEI or a mixture thereof. Preferably they have essentially the structure SAPO 18 or SAPO 34 or a mixture thereof.

The above metalloaluminophosphate (MeAPO) molecular sieve can be made by a method which comprises:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$, said reaction mixture having a composition expressed in terms of molar oxide ratios of:

$TEMP/Al_2O_3$=0.3-5, more desirable 0.5-2

$MeO_2/Al_2O_3$=0.005-2.0, more desirable 0.022-0.8

$P_2O_5/Al_2O_3$=0.5-2, more desirable 0.8-1.2

$TIA/Al_2O_3$=3-30, more desirable 6-20 b) crystallizing the above reaction mixture thus formed until crystals of the metalloaluminophosphate are formed,
c) recovering a solid reaction product,
d) washing it with water to remove the TIA and
e) calcinating it to remove the organic template.

In an advantageous embodiment $TEMP/Al_2O_3$=0.5-2; $MeO_2/Al_2O_3$=0.022-0.8; $P_2O_5/Al_2O_3$=0.8-1.2 and $TIA/Al_2O_3$=6-20.

In a first preferred embodiment $TEMP/Al_2O_3$=0.5-2; $MeO_2/Al_2O_3$=0.022-0.7; $P_2O_5/Al_2O_3$=0.8-1.2 and $TIA/Al_2O_3$=6-20.

In a second preferred embodiment $TEMP/Al_2O_3$=0.7-2; $MeO_2/Al_2O_3$=0.05-0.7; $P_2O_5/Al_2O_3$=0.8-1.2 and $TIA/Al_2O_3$=6-20.

In a third preferred embodiment $TEMP/Al_2O_3$=0.7-2; $MeO_2/Al_2O_3$=0.05-0.6; $P_2O_5/Al_2O_3$=0.8-1.2 and $TIA/Al_2O_3$=6-20.

The present invention also relates to catalysts consisting of the above MeAPO molecular sieves or comprising the above MeAPO molecular sieves.

The present invention also relates to a process for making an olefin product from an oxygen-containing, halogenide-containing or sulphur-containing organic feedstock wherein said oxygen-containing, halogenide-containing or sulphur-containing organic feedstock is contacted with the above catalyst under conditions effective to convert the oxygen-containing, halogenide-containing or sulphur-containing organic feedstock to olefin products.

According to an advantageous embodiment of the invention said olefin products are fractionated to form a stream comprising essentially ethylene and at least a part of said stream is recycled on the catalyst to increase the propylene production and then the flexibility of ethylene vs propylene production. Advantageously the ratio of ethylene to the oxygen-containing, halogenide-containing or sulphur-containing organic feedstock is 1.8 or less.

DETAILED DESCRIPTION OF THE INVENTION

With regards to the plate crystal morphology, said plates have advantageously the shape of a simple polygon comprised in a square. The square's length is named W. The MeAPO molecular sieves of this invention have predominantly a plate crystal morphology. By predominantly is meant advantageously greater than 50% of the crystals. Preferably at least 70% of the crystals have a plate morphology and most preferably at least 90% of the crystals have a plate morphology. About "essentially" referring to the CHA or AEI structure it means that advantageously more than 80% by weight, preferably more than 90%, of the MeAPO of the invention has the structure CHA or AEI or a mixture thereof. About "essentially" referring to the SAPO 18 or SAPO 34 structure it means that advantageously more than 80% by weight, preferably more than 90%, of the MeAPO of the invention has the structure SAPO 18 or SAPO 34 or a mixture thereof.

With regards to Me, it is advantageously a metal selected from the group consisting of silicon, germanium, magnesium, zinc, iron, cobalt, nickel, manganese, chromium and mixtures thereof. Preferred metals are silicon, magnesium and cobalt with silicon or germanium being especially preferred.

With regards to the TIA, mention may be made, by way of example, of 1,2-propanediol, 1,3-propanediol, methanol, ethanol, propanol, isopropanol, butanol, glycerol or ethylene glycol.

With regards to the organic templating agent, it can be any of those heretofore proposed for use in the synthesis of conventional zeolitic aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di and tri-amines are advantageously utilized, either alone or in combination with a quaternary ammonium compound or other templating compound. Representative templating agents include tetramethylammonium, tetraethylammonium, tetrapropylammonium or tetrabutylammonium cations; di-n-propylamine, tripropylamine, triethylamine; diethylamine, triethanolamine; piperidine; morpholine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo(2,2,2)octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Advantageously organic templating agent is selected among tetraethylammonium hydroxide (TEAOH), diisopropylethylamine (DPEA), tetraethyl ammonium salts, cyclopentylamine, aminomethyl cyclohexane, piperidine, triethylamine, diethylamine, cyclohexylamine, triethyl hydroxyethylamine, morpholine, dipropylamine, pyridine, isopropylamine di-n-propylamine, tetra-n-butylammonium hydroxide, diisopropylamine, di-n-propylamine, n-butylethylamine, di-n-butylamine, and di-n-pentylamine and combinations thereof. Preferably the template, is a tetraethyl ammonium compound selected from the group of tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Most preferably, the template is tetraethyl ammonium hydroxide.

With regards to the reactive inorganic source of $MeO_2$ essentially insoluble in the TIA and relating to silicon, non-limiting examples of useful inorganic silicon source materials non-soluble in alcohols include, fumed silica, aerosol, pyrogenic silica, precipitated silica and silica gel.

With regards to the reactive sources of $Al_2O_3$, it can be any aluminum species capable of being dispersed or dissolved in an aqueous synthesis solution. Useful sources of alumina are one or more sources selected from the group consisting of the following: hydrated alumina, organo alumina, in particularly $Al(OiPr)_3$, pseudo-boehmite, aluminum hydroxide, colloidal alumina, aluminium halides, aluminium carboxylates, aluminium sulfates and mixtures thereof.

With regards to the reactive sources of $P_2O_5$, it can be one or more sources selected from the group consisting of phosphoric acid; organic phosphates, such as triethyl phosphate, tetraethyl-ammonium phosphate; aluminophosphates; and mixtures thereof. The phosphorous source should also be capable of being dispersed or dissolved in an alcohol synthesis solution.

The metalloaluminophosphates of the invention can be prepared by the usual methods of the molecular sieves synthesis technology provided it is in accordance with the above cited ratios. The reaction mixture is in the form of a gel. The ratios $MeO_2/Al_2O_3$ and $P_2O_5/Al_2O_3$ are selected among the above described advantageous and preferred ratios and are in accordance with the advantageous and preferred y, z and k described above. By way of example to make a MeAPO having the y, z and k according to the second preferred embodiment one has to use the ratios of the ingredients according to the second preferred embodiment of the method to make said MeAPO.

With regards to the step b), the reaction mixture obtained by mixing the reactive sources of alumina, $MeO_2$, phosphorus, organic templating agent and TIA is submitted to autogenous pressure and elevated temperature. The reaction mixture is heated up to the crystallization temperature that may range from about 120° C. to 250° C., preferably from 130° C. to 225° C., most preferably from 150° C. to 200° C. Heating up to the crystallization temperature is typically carried for a period of time ranging from about 0.5 to about 16 hours, preferably from about 1 to 12 hours, most preferably from about 2 to 9 hours. The temperature may be increased stepwise or continuously. However, continuous heating is preferred. The reaction mixture may be kept static or agitated by means of tumbling or stirring the reaction vessel during hydrothermal treatment. Preferably, the reaction mixture is tumbled or stirred, most preferably stirred. The temperature is then maintained at the crystallization temperature for a period of time ranging from 2 to 200 hours. Heat and agitation is applied for a period of time effective to form crystalline product. In a specific embodiment, the reaction mixture is kept at the crystallization temperature for a period of from 16 to 96 hours.

With regards to the step c), the usual means can be used. Typically, the crystalline molecular sieve product is formed as a slurry and can be recovered by standard means, such as by sedimentation, centrifugation or filtration.

With regards to the step d), the separated molecular sieve product is washed, recovered by sedimentation, centrifugation or filtration and dried.

With regards to the step e), calcination of molecular sieves is known per se. As a result of the molecular sieve crystallization process, the recovered molecular sieve contains within its pores at least a portion of the template used. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system.

Additionally, if during the synthesis alkaline or alkaline earth metals have been used, the molecular sieve might be subjected to an ion-exchange step. Conventionally, ion-exchange is done in aqueous solutions using ammonium salts or inorganic acids.

Once the molecular sieve is made, it can be used as itself as a catalyst. In another embodiment it can be formulated into a catalyst by combining the molecular sieve with other materials that provide additional hardness or catalytic activity to the finished catalyst product. This invention also relates to said catalysts consisting of the MeAPO molecular sieves of this invention or comprising the MeAPO molecular sieves of this invention.

Materials which can be blended with the molecular sieve can be various inert or catalytically active materials, or various binder materials. These materials include compositions such as kaolin and other clays, various forms of rare earth metals, alumina or alumina sol, titania, zirconia, quartz, silica or silica sol, and mixtures thereof. These components are effective in densifying the catalyst and increasing the strength of the formulated catalyst. When blended with non-metalloaluminophosphate molecular sieve materials, the amount of MeAPO of the present invention, which is contained in the final catalyst product ranges from 10 to 90 weight percent of the total catalyst, preferably 20 to 70 weight percent of the total catalyst.

The MeAPO molecular sieves of the present invention can be used to dry gases and liquids; for selective molecular separation based on size and polar properties; as ion-exchangers; as catalysts in cracking, hydrocracking, disproportionation, alkylation, isomerization, oxidation; as chemical carriers; in gas chromatography; and in the petroleum industry to remove normal paraffins from distillates. More precisely they are useful as catalysts in a variety of processes including cracking of, for example, a naphtha feed to light olefin(s) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a oligomer product; dewaxing of, for example, hydrocarbons to remove straight chain paraffins; absorption of, for example, alkyl aromatic compounds for separating out isomers thereof; oligomerization of, for example, straight and branched chain olefin(s); and the synthesis of monoalkylamines and dialkylamines.

The MeAPO of the present invention are particularly suited for the catalytic conversion of oxygen-containing, halogenide-containing or sulphur-containing organic compounds to hydrocarbons. Accordingly, the present invention also relates to a method for making an olefin product from an oxygen-containing, halogenide-containing or sulphur-containing organic feedstock wherein said oxygen-containing, halogenide-containing or sulphur-containing organic feedstock is contacted with the catalyst of this invention comprising the molecular sieve of this invention under conditions effective to convert the oxygen-containing, halogenide-containing or sulphur-containing organic feedstock to olefin products. In this process a feedstock containing an oxygen-containing, halogenide-containing or sulphur-containing organic compound contacts the above described catalyst in a reaction zone of a reactor at conditions effective to produce light olefins, particularly ethylene and propylene. Typically, the oxygen-containing, halogenide-containing or sulphur-containing organic feedstock is contacted with the catalyst when the oxygen-containing, halogenide-containing or sulphur-containing organic compounds is in vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 575° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of transport beds, although a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised or moving bed systems. The commercial scale reactor systems can be operated at a weight hourly space velocity (WHSV) of from 0.1 $hr^{-1}$ to 1000 $hr^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

The oxygenate feedstock is any feedstock containing a molecule or any chemical having at least an oxygen atom and capable, in the presence of the above MeAPO catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts.

Analogously to these oxygenates, compounds containing sulphur or halides may be used. Examples of suitable compounds include methyl mercaptan; dimethyl sulfide; ethyl mercaptan; di-ethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

The method of making the olefin products from an oxygenate feedstock can include the additional step of making the oxygenate feedstock from hydrocarbons such as oil, coal, tar sand, shale, biomass and natural gas. Methods for making oxygen-containing, halogenide-containing, sulphur-containing organic feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized to form polyolefins, particularly polyethylenes and polypropylenes.

EXAMPLES

In the following examples:
EG means ethylene glycol,
Eth means ethanol,
MeOH means methanol,
XRD means X ray diffraction,
SEM means scanning electron microscopy,
Aerosil 200® is a fumed silica supplied by Degussa.

Examples 1-3

A reaction mixture of TIA, phosphoric acid (85% in water) and TEAOH solution (40% in water) was prepared in a teflon vessel. In this solution were added corresponding amount of Al source and Si-source respectively. This slurry was mixed until homogeneous for about 30 min at room temperature. Then the teflon vessel was put into stainless autoclave. This autoclave was closed and kept at elevated temperature under stirring. After cooling to room temperature, a sample was taken, washed and dried. Separation of the solid from the liquid phase after synthesis was performed by centrifugation. Separated solid was dried at 110° C. overnight and calcined in air flow at 600° C. for 10 h. Proportions and operating conditions are in the following table. This procedure was applied for the all examples.

Figure 1A:
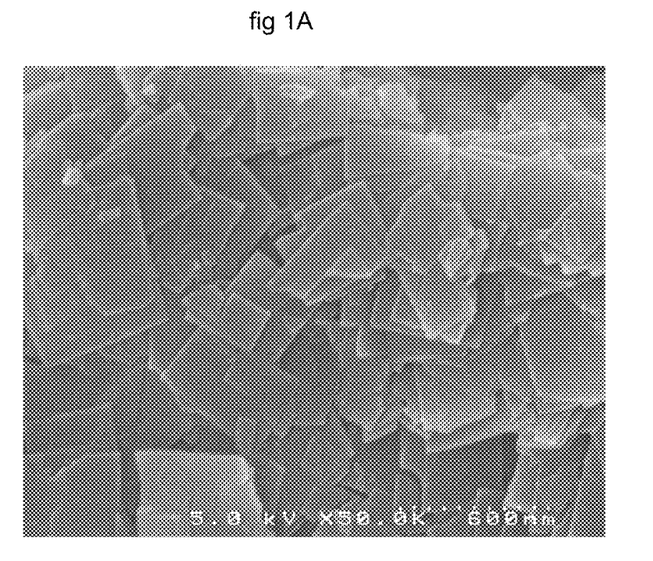
FIG. 1 is 2 SEM of the product of Example 1.
Figure 1B:
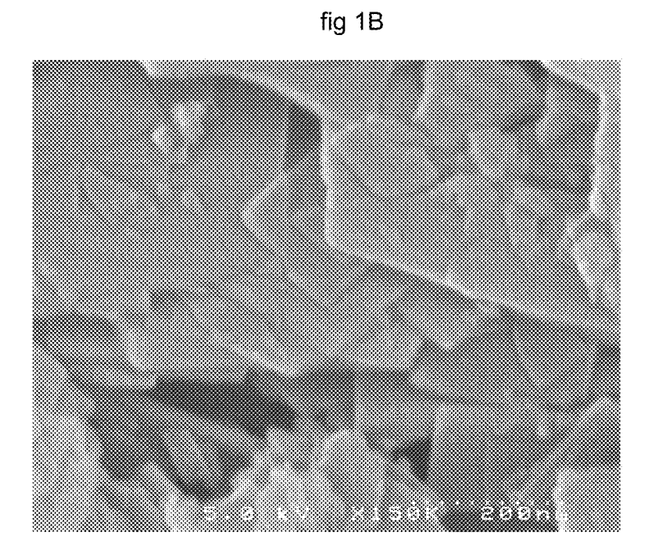

|  | Example | |
|---|---|---|
|  | 1 | 2 |
| molar composition | 1 TEAOH/0.1SiO$_2$/1P$_2$O$_5$/ 1Al$_2$O$_3$/12TIA | |
| TEAOH (35% in water), g | 7.01 | 7.04 |
| Al isopropoxide 98%, g | 6.95 | 6.94 |
| TIA, g | 12.41 EG | 9.22 Eth |
| Aerosil 200, g | 0.10 | 0.11 |
| H$_3$PO$_4$ (85% in water), g | 3.84 | 3.96 |
| Conditions | 160° C., 3 days | |
| XRD | SAPO-18 | SAPO-18 |
| SEM | Lamellar FIG. 1 | Lamellar |

|  | Example 3 |
|---|---|
| molar composition | 1 TEAOH/0.1 SiO$_2$/0.9 P$_2$O$_5$/0.9 Al$_2$O$_3$/12 TIA |
| TEAOH (40% in water), g | 28.03 |
| Al isopropoxide 98%, g | 27.82 |
| TIA, g | 27.81 MeOH |
| Aerosil 200, g | 0.50 |
| H$_3$PO$_4$ (85% in water), g | 15.80 |
| Conditions | 160° C., 3 days |
| XRD | SAPO-18 |
| SEM | Lamellar |

Examples 4-6

|  | Example 4 |
|---|---|
| molar composition | 1 TEAOH/0.3 SiO$_2$/1 P$_2$O$_5$/1 Al$_2$O$_3$/12 TIA |
| TEAOH (35% in water), g | 28.00 |
| Al isopropoxide 98%, g | 27.80 |
| TIA, g | 50.15 EG |
| Aerosil 200 g | 1.34 |
| H$_3$PO$_4$ (85% in water), g | 15.30 |
| Conditions | 3 days, 160° C. |
| XRD | SAPO-18 |
| SEM | Lamellar |

|  | Example | |
|---|---|---|
|  | 5 | 6 |
| molar composition | 1 TEAOH/0.3SiO$_2$/0.9P$_2$O$_5$/ 0.9Al$_2$O$_3$/12TIA | |
| TEAOH (40% in water), g | 28.03 | 28.03 |
| Al isopropoxide 98%, g | 27.82 | 27.82 |
| TIA, g | 39.99 Eth | 27.81 MeOH |
| Aerosil 200 g | 1.50 | 1.50 |
| H$_3$PO$_4$ (85% in water), g | 15.80 | 15.80 |
| Conditions | 3 days, 160° C. | |
| XRD | SAPO-18 | SAPO-34 |
| SEM | Lamellar | Lamellar |

Examples 7-8

|   | Example 7 |
|---|---|
| molar composition | 1 TEAOH/0.6SiO$_2$/1P$_2$O$_5$/1Al$_2$O$_3$/12TIA |
| TEAOH (35% in water), g | 28.10 |
| Al isopropoxide 98%, g | 27.80 |
| TIA g | 50.08 EG |
| Aerosil 200, g | 2.50 |
| H$_3$PO$_4$ (85% in water), g | 15.30 |
| Conditions | 3 days, 160° C. |
| XRD | SAPO-18 |
| SEM | Lamellar |

Figure 2:
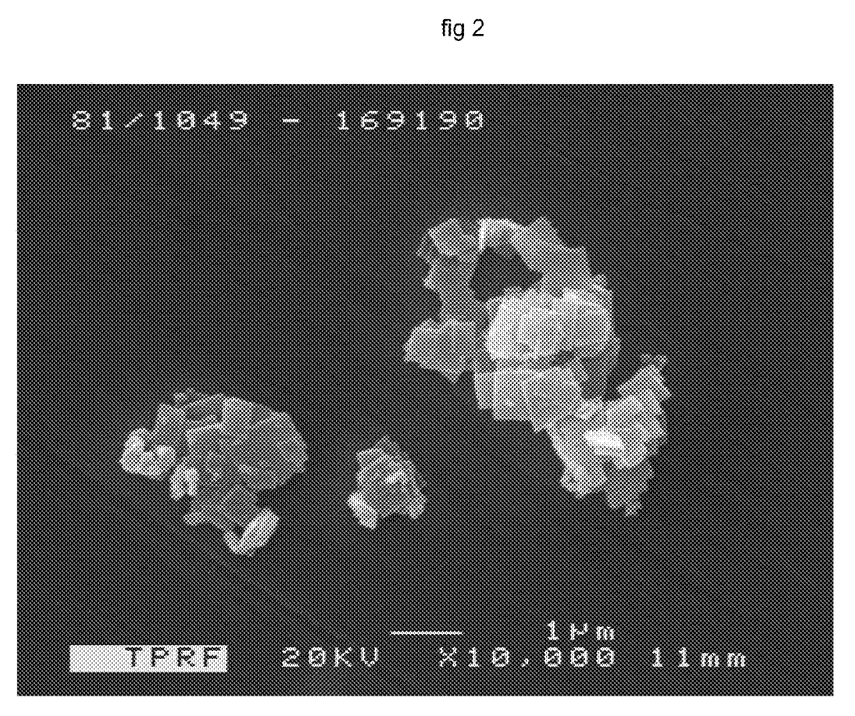
FIG. 2 is a SEM of the product of Example 8.

|   | Example 8 |
|---|---|
| molar composition | 1 TEAOH/0.6SiO$_2$/0.9P$_2$O$_5$/0.9Al$_2$O$_3$/12TIA |
| TEAOH (40% in water), g | 28.03 |
| Al isopropoxide 98%, g | 27.82 |
| TIA g | 39.99 Eth |
| Aerosil 200, g | 3.06 |
| H$_3$PO$_4$ (85% in water), g | 15.80 |
| Conditions | 3 days, 160° C. |
| XRD | SAPO-34 |
| SEM | Lamellar FIG. 2 |

Example 9

Synthesis at Higher Temperature

|   | Example 9 |
|---|---|
| molar composition | 1 TEAOH/0.3SiO$_2$/1P$_2$O$_5$/1Al$_2$O$_3$/12TIA |
| TEAOH (35% in water), g | 28.10 |
| Al isopropoxide 98%, g | 27.80 |
| TIA g | 50.08 EG |
| Aerosil 200 g | 1.34 |
| H$_3$PO$_4$ (85% in water), g | 15.50 |
| Conditions | 3 days, 190° C. |
| XRD | SAPO-18 |
| SEM | Lamellar |

Examples 10-11

Reduced Amount of TIA

|   | Example 10 | Example 11 |
|---|---|---|
| molar composition | 1 TEAOH/0.1SiO$_2$/1P$_2$O$_5$/1Al$_2$O$_3$/6TIA | |
| TEAOH (35% in water), g | 14.02 | 11.06 |
| Al isopropoxide 98%, g | 13.89 | 10.91 |
| TIA g | 12.54 EG | 7.25 Eth |
| Aerosil 200, g | 0.20 | 0.16 |
| H$_3$PO$_4$ (85% in water), g | 7.69 | 6.12 |
| XRD | SAPO-18 | SAPO-18 |
| SEM | Lamellar | Lamellar |

Example 12

Synthesis with Reduced Amount of Template

|   | Example 12 |
|---|---|
| molar composition of gel | 0.7/TEAOH/0.1SiO$_2$/1Al$_2$O$_3$/15EG/1P$_2$O$_5$ |
| TEAOH (35% in water), g | 9.81 |
| Al isopropoxide 98%, g | 13.89 |
| TIA, g | 31.35 EG |
| Aerosil 200, g | 0.20 |
| H$_3$PO$_4$ (85% in water), g | 7.69 |
| Conditions | 160° C., 4 days |
| XRD | SAPO-18 |
| SEM | Lamellar |

Example 13

Synthesis with Increased Amount of Template in Presence of EG

Figure 3A:
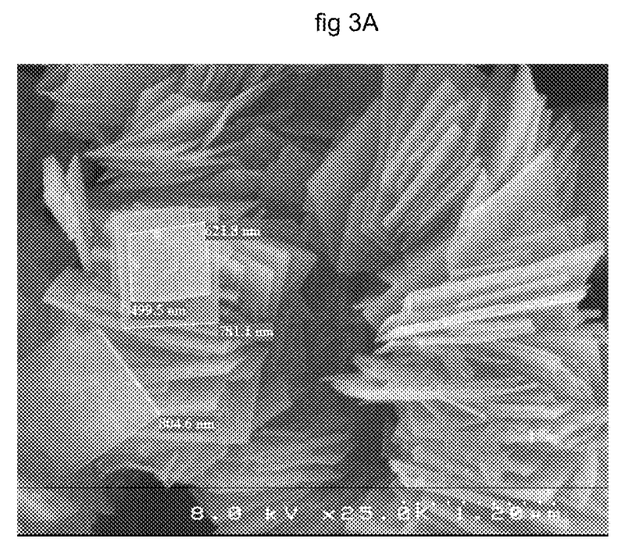
FIG. 3 is 2 SEM of the product of Example 13.
Figure 3B:
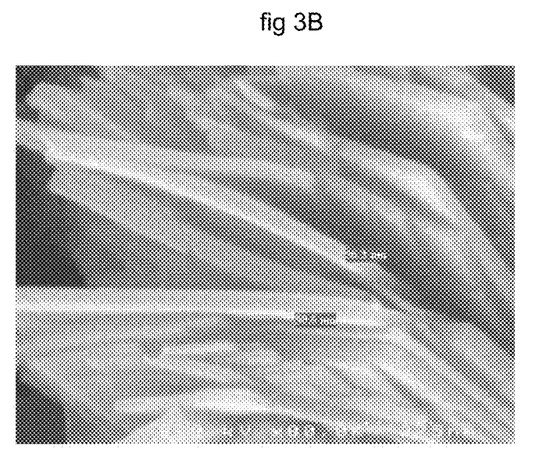

|   | Example 13 |
|---|---|
| molar composition | 2TEAOH/0.1SiO$_2$/1Al$_2$O$_3$/1P$_2$O$_5$/6EG |
| TEAOH (35% in water), g | 28.00 |
| Al isopropoxide 98%, g | 13.90 |
| TIA, g | 12.54 EG |
| Aerosil 200, g | 0.20 |
| H$_3$PO$_4$ (85% in water), g | 7.69 |
| Conditions | 160° C., 4 days |
| XRD | SAPO-18 |
| SEM | Lamellar FIG. 3 |

Example 14

Synthesis at Lower Si-Content

|   | Example 14 |
|---|---|
| molar composition | 1TEAOH/0.05 SiO$_2$/1Al$_2$O$_3$/1P$_2$O$_5$/12EG |
| TEAOH (35% in water), g | 14.00 |
| Al isopropoxide 98%, g | 13.90 |
| TIA, g | 25.08 EG |
| Aerosil 200, g | 0.10 |
| H$_3$PO$_4$ (85% in water), g | 7.7 |
| Conditions | 160° C., 4 days |
| XRD | SAPO-18 |
| SEM | Lamellar |

Comparative Example I

The essential of this recipe: the source of Si must be soluble in alcohol. In the present invention all Si sources are not soluble in TIA.

Synthesis of SAPOs in presence of alcohol with organic source of Si according to U.S. Pat. No. 6,540,970 protocol:

|  | Example comparative example I |
|---|---|
| Recipe | U.S. Pat. No. 6,540,970 B1 |
| molar composition | $2TEAOH/0.1SiO_2/1Al_2O_3/1P_2O_5/50\ H_2O/8\ Eth$ |
| $H_2O$, g | 19.90 |
| TEAOH (35% in water), g | 60.00 |
| Al source (catapal B), g a hydrated alumina | 10.04 |
| Ethanol, g | 26.28 |
| Si source TEOS, g | 1.52 |
| $H_3PO_4$ (85% in water), g | 16.44 |
| Conditions | 195° C., 1 day |
| XRD | SAPO-34/18 |
| SEM | Cubic crystal FIG. 4 |

Figure 4:
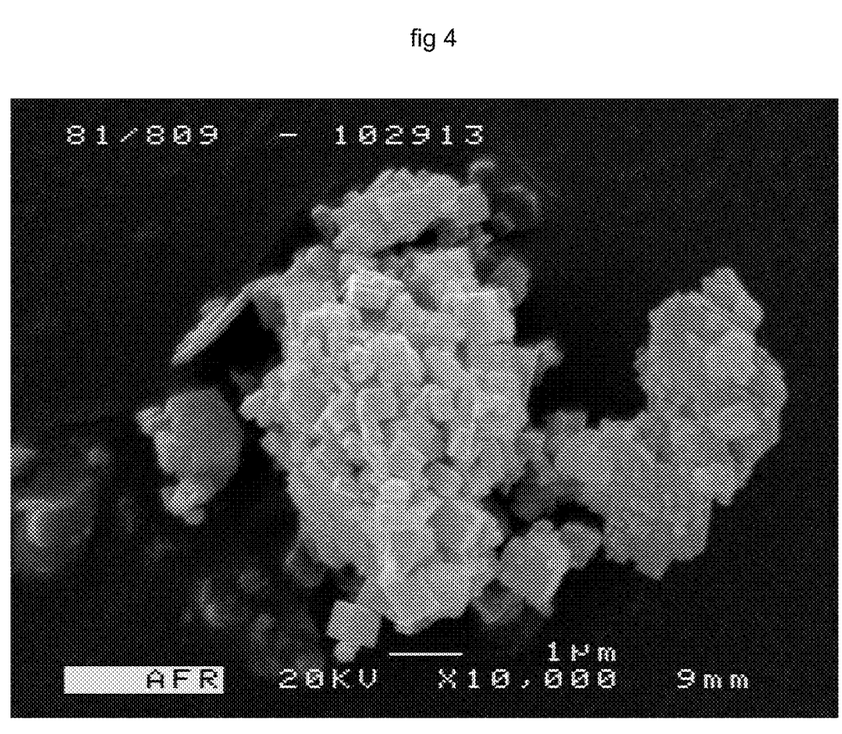
FIG. 4 is a SEM of the product of Comparative Example I.

Morphology of the samples synthesized according to this recipe is different from lamellar. Indeed, a very particular spheroidal morphology has been described in this patent for SAPO-34 sample. The crystallites have a width, at their largest dimension, of from about 0.5 μm to about 30 μm.

Reproduction of example for SAPO-18 synthesis led to materials with cubic crystals.

Comparative Example II

Synthesis of SAPO-18 (Chen's Recipe)
- Verified Syntheses of Zeolitic Materials, H. Robson, Elsevier, p. 81,
- Catalysis Letters 28 (1994) 241-248
- J. Chem. Soc., Chem. Comm., 1994, 603-604
- J. Phys. Chem. 1994, 98, 10216-10224

Figure 5A:
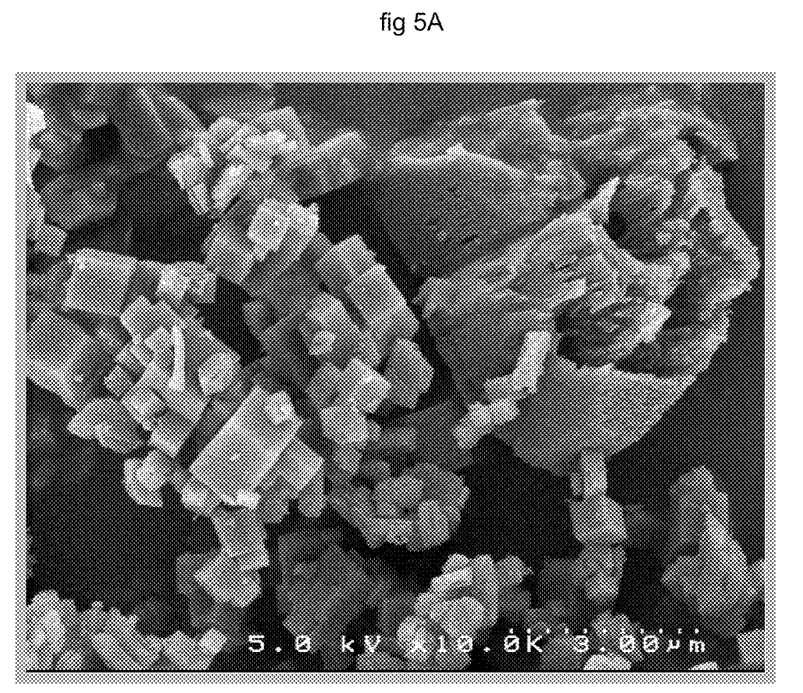
FIG. 5 is 2 SEM of the product of Comparative Example II.
Figure 5B:
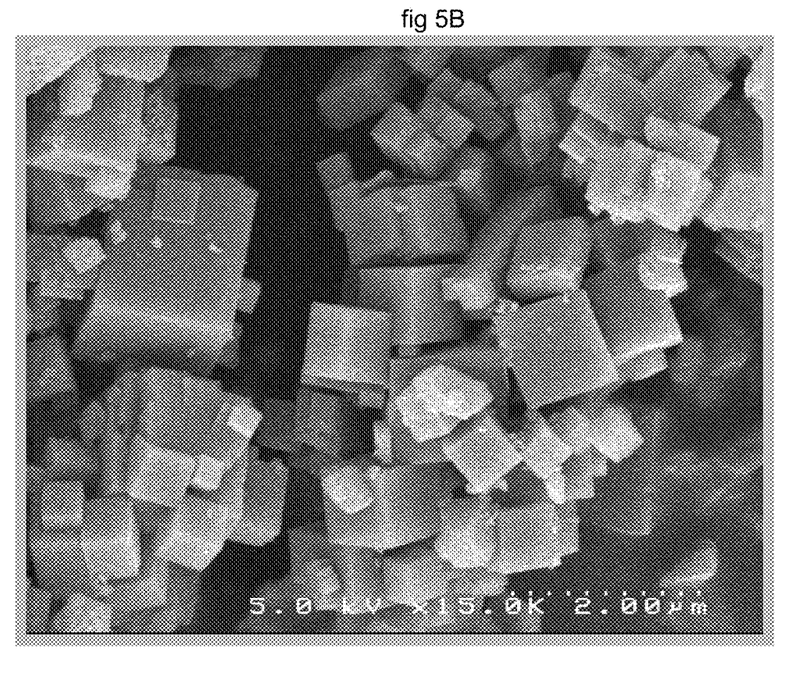
Figure 6A:
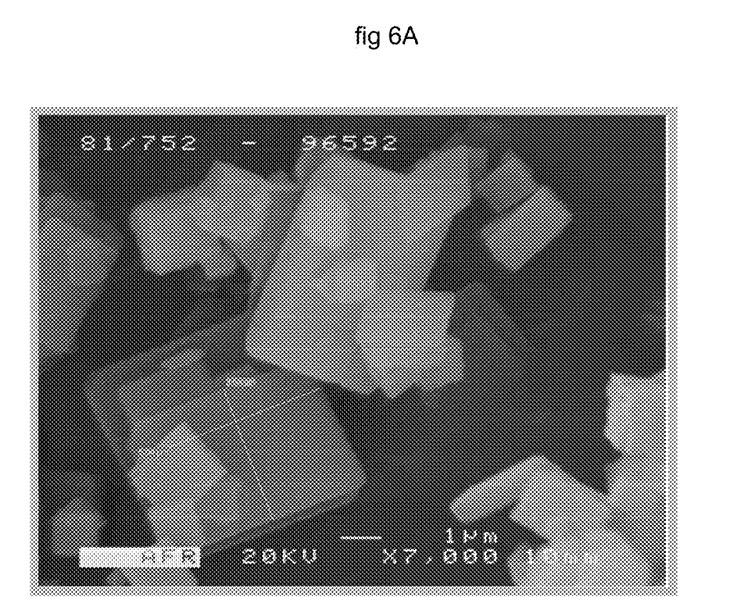
FIG. 6 is 4 SEM of the product of Comparative Example IIIa.
Figure 6B:
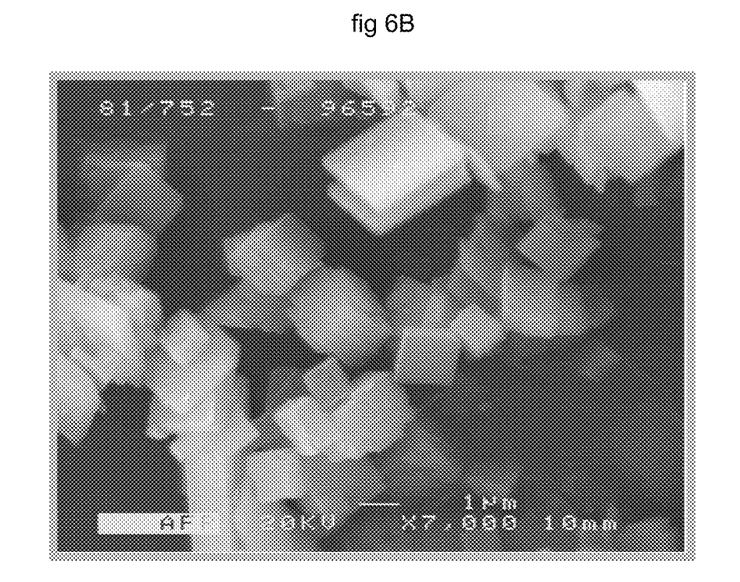
Figure 6C:
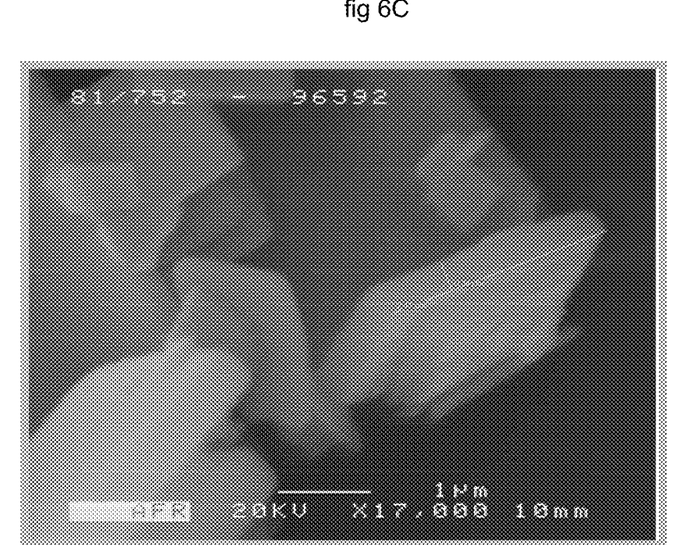
Figure 6D:
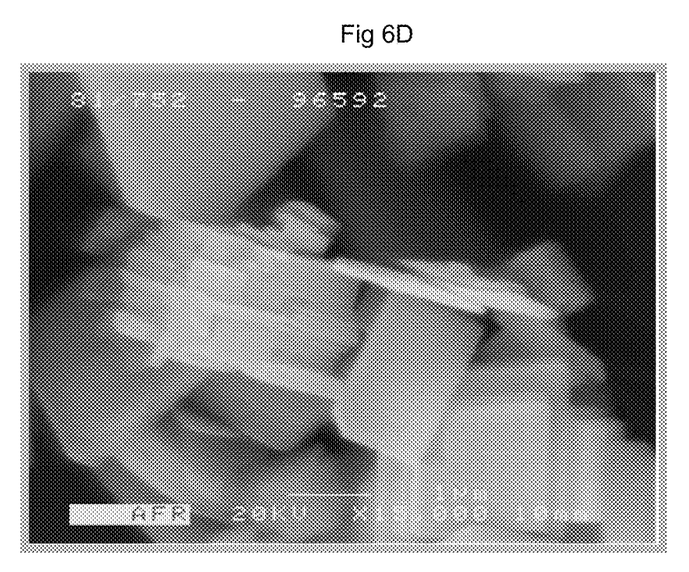

|  | Example Comparative ex II |
|---|---|
| Molar composition | $0.4SiO_2:1Al_2O_3:0.9P_2O_5:50H_2O:1.9\ DPEA$ |
| $H_2O$, g | 66.92 |
| $H_3PO_4$ (85% in water), g | 16.73 |
| Al source (catapal B), g a hydrated alumina | 11.35 |
| Aerosil 200, g | 1.96 |
| DPEA, g | 20.00 |
| Conditions: | 160° C., 7 days |
| XRD | SAPO-18 |
| SEM | cubes FIG. 5 |

Comparative Example III

Synthesis of SAPOs According to Recipe of U.S. Pat. No. 6,334,994 at High and Low Si Content

Figure 7:
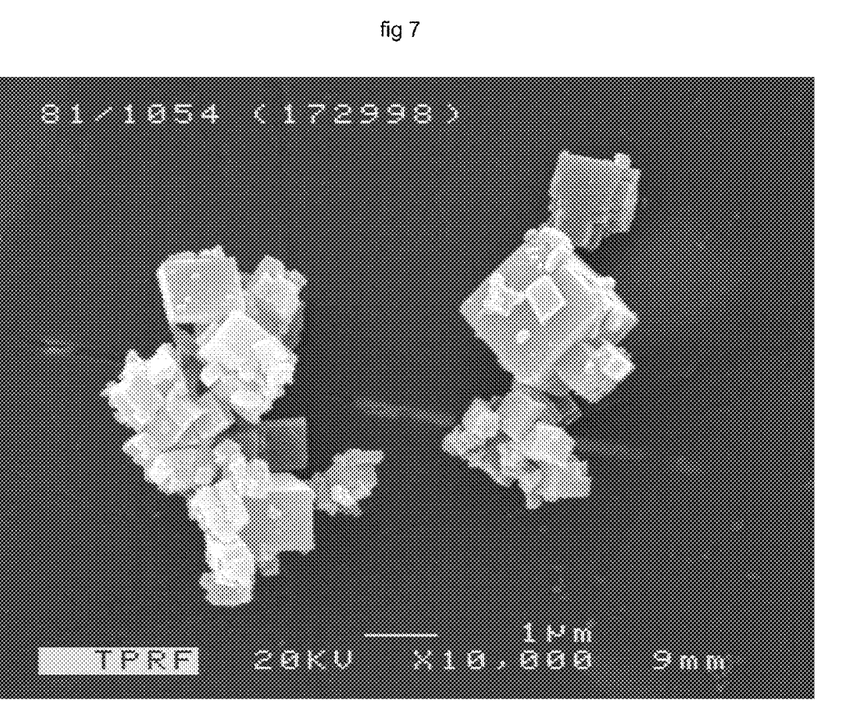
FIG. 7 is a SEM of the product of Comparative Example IIIb.

|  | Example | |
|---|---|---|
|  | Comparative ex IIIa | Comparative ex IIIb |
| Recipe reference | U.S. Pat. No. 6,334,994 | Microporous Mesoporous 1999, 29, 159 |
| molar composition | $0.075SiO_2/Al_2O_3/$ $0.98P_2O_5/2\ TEAOH$ | $0.3SiO_2/Al_2O_3/$ $0.98P_2O_5/2\ TEAOH$ |
| $H_2O$, g | 18.06 | 36.08 |
| Al isopropoxide 98%, g | 13.80 | 27.23 |
| $H_3PO_4$ (85% in water), g | 7.52 | 15.17 |
| HCl, g | 0.12 | 0.20 |
| Ludox AS 40 (40% silica), g | 0.54 | 4.00 |
| TEAOH (35% in water), g | 28.20 | 56.08 |
| XRD | SAPO-18 | SAPO-34 |
| SEM | laminated cubes FIG. 6 | cubes FIG. 7 |

Comparative Example IV

U.S. Pat. No. 6,953,767 B2

Inventors in the U.S. Pat. No. 6,953,767B2 described a synthesis of SAPOs phase mixed structure. 18/34 phase ratio was tuned by changing the turning rate of autoclave during the synthesis.

The results showed, that phase composition is reproducible but the morphology was not lamellar.

Figure 8:
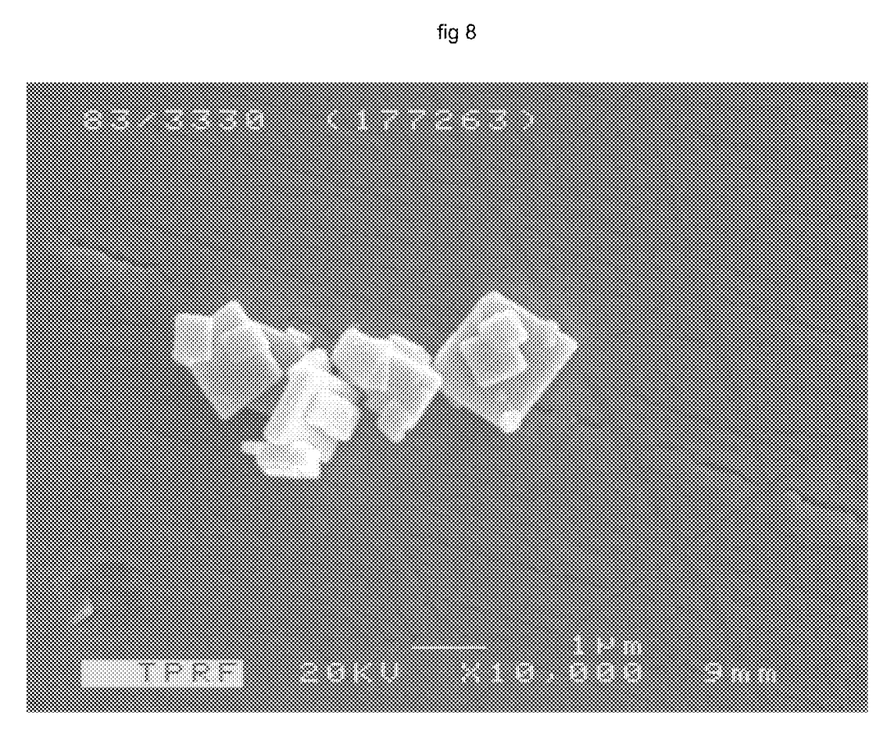
FIG. 8 is a SEM of the product of Comparative Example IV.

|  | Example Comparative ex IV same as ex 1 of U.S. Pat. No. 6,953,767 B2 |
|---|---|
| molar composition | $0.15SiO_2/1Al_2O_3/1P_2O_5/1TEAOH/35\ H_2O$ |
| Conditions | 175° C., 8 h |
| rotation rate, rpm | 60 |
| $H_2O$, g | 32.13 |
| Alumina (Condea Pural SB), g | 19.85 |
| $H_3PO_4$, (85% in water), g | 33.55 |
| Ludox AS 40 (40% silica), g | 3.32 |
| TEAOH (35% in water), g | 61.40 |
| TOTAL weight, g | 150.25 |
| XRD | AEI/CHA~0.2 |
| SEM | laminated cubes FIG. 8 |

Example 15

MTO

Catalyst tests were performed on 2 g catalyst samples with a essentially pure methanol feed at 450° C., at a pressure of 0.5 barg and $WHSV=1.6\ h^{-1}$, in a fixed-bed, down flow stainless-steel reactor. Catalyst powders was pressed into wafers and crushed to 35-45 mesh particles. Prior to catalytic run all catalysts were heated in flowing $N_2$ (5 Nl/h) up to the reaction temperature. Analysis of the products has been performed on-line by a gas chromatograph equipped with a capillary column. Catalytic performances of MeAPOs molecular sieves were compared at 100% of methanol conversion and maximum of catalyst activity just before appearance of DME in the effluent. The results are in table 1 hereunder. The values in table 1 are the effluent of the MTO reactor and are the weight percent on carbon basis.

TABLE 1

|  | SAPO-18 | SAPO-18 | SAPO-18 | SAPO-18 | SAPO-34/18 | SAPO-18 |
|---|---|---|---|---|---|---|
| Morphology | lamellar | lamellar | lamellar | lamellar | cubic | cubic |
| catalyst of ex No | Ex 1 | Ex 5 | Ex 10 | Ex 14 | comp ex I | comp ex II |
| Methane in the effluent | 2.8 | 1.7 | 2.9 | 2.8 | 4.7 | 4.9 |
| Paraffins (comprises the C1 above) | 8.7 | 3.6 | 5.4 | 8.2 | 10.1 | 9.3 |
| Olefins | 90.7 | 95.9 | 94.2 | 91.0 | 85.4 | 85.9 |
| Dienes | 0.4 | 0.2 | 0.4 | 0.2 | 3.8 | 4.2 |
| Aromatics | 0.1 | 0.3 | 0.1 | 0.5 | 0.7 | 0.6 |
| Purity C2's | 99 | 99 | 99 | 98 | 95 | 97 |
| Purity C3's | 99 | 99 | 99 | 99 | 97 | 97 |
| C3/C2 | 1.2 | 1.2 | 1.2 | 1.3 | 1.0 | 1.0 |
| C2 + C3 | 70.4 | 72.7 | 74.3 | 73.2 | 73.2 | 70.8 |
| ethylene | 32.1 | 33.5 | 34.1 | 31.7 | 36.0 | 35.1 |
| propylene | 38.3 | 39.2 | 40.2 | 41.5 | 37.3 | 35.7 |

Example 16

Catalyst tests were performed on 2 g catalyst samples with a methanol/$H_2O$: 70/30 feed at 450° C., at a pressure of 0.2 barg, WHSV=2.9 $h^{-1}$, in a fixed-bed, down flow stainless-steel reactor. Catalyst powders was pressed into wafers and crushed to 35-45 mesh particles. Prior to catalytic run all catalysts were heated in flowing $N_2$ (5 Nl/h) up to the reaction temperature. Analysis of the products has been performed on-line by a gas chromatograph equipped with a capillary column. Catalytic performances of SAPOs molecular sieves were compared at 100% of methanol conversion and maximum of catalyst activity just before appearance of DME in the effluent. The results are in table 2 hereunder. The values in table 2 are the effluent of the MTO reactor and are the weight percent on carbon basis.

TABLE 2

|  | SAPO-18 | SAPO-34 |
|---|---|---|
| Morphology | lamellar | laminated cube |
|  | Ex 12 | comp ex IIIa |
|  | 81/742 | 81/752 |
| Methane in the effluent | 2.0 | 2.5 |
| Purity C2's | 100 | 100 |
| Purity C3's | 100 | 98 |
| C3/C2 | 1.2 | 1.0 |
| C2 + C3 | 78.0 | 80.0 |
| ethylene | 36.0 | 41.0 |
| propylene | 42.0 | 39.0 |

The invention claimed is:

1. A metalloaluminophosphate (MeAPO) molecular sieve comprising:
   a lamellar crystal morphology having an empirical chemical composition on an anhydrous basis, after synthesis and calcination, expressed by the formula $H_xMe_yAl_zP_kO_2$; wherein,
   the sum of y plus z plus k equals 1.0;
   x is less than or equal to y;
   y has a value ranging from 0.0008 to 0.4;
   z has a value ranging from 0.25 to 0.67;
   k has a value ranging from 0.2 to 0.67; and
   said molecular sieve having predominantly a plate crystal morphology having a width (W) and a thickness (T) wherein W/T is greater than or equal to 10, wherein the process of preparing the MeAPO molecular sieve includes the use of a texture influencing agent.

2. The MeAPO molecular sieve of claim 1, wherein y has a value from 0.005 to 0.18.

3. The MeAPO molecular sieve of claim 1, wherein z has a value from 0.38 to 0.55.

4. The MeAPO molecular sieve of claim 1, wherein k has a value from 0.36 to 0.54.

5. The MeAPO molecular sieve of claim 1, wherein Me is silicon.

6. The MeAPO molecular sieve of claim 1, wherein T is less than or equal to 0.15 μm.

7. The MeAPO molecular sieve of claim 1, wherein T is less than or equal to 0.10 μm.

8. The MeAPO molecular sieve of claim 1, wherein T is less than or equal to 0.08 μm.

9. The MeAPO molecular sieve of claim 1, wherein T ranges from 0.01 to 0.07 μm.

10. The MeAPO molecular sieve of claim 1, wherein T ranges from 0.04 to 0.07 μm.

11. The MeAPO molecular sieve of claim 1, wherein W/T ranges from 10 to 100.

12. The MeAPO molecular sieve of claim 1, wherein the structure is essentially CHA or AEI or a mixture thereof.

13. The MeAPO molecular sieve of claim 1, wherein the structure is essentially SAPO 18 or SAPO 34 or a mixture thereof.

14. A catalyst comprising:
   a MeAPO molecular sieve having a lamellar crystal morphology with an empirical chemical composition on an anhydrous basis, after synthesis and calcination, expressed by the formula $H_xMe_yAl_zP_kO_2$; wherein,
   y+z+k=1 x is less than or equal to y;
   y has a value ranging from 0.0008 to 0.4;
   z has a value ranging from 0.25 to 0.67;
   k has a value ranging from 0.2 to 0.67; and
   said molecular sieve having predominantly a plate crystal morphology having a width (W) and a thickness (T) wherein W/T is greater than or equal to 10, wherein the process of preparing the MeAPO molecular sieve includes the use of a texture influencing agent.

15. A process for making an olefin product comprising:
   contacting an oxygenate feedstock with a catalyst under conditions effective to convert the oxygenate feedstock to olefin products; the catalyst comprising a MeAPO molecular sieve having a lamellar crystal morphology with an empirical chemical composition on an anhydrous basis, after synthesis and calcination, expressed by the formula $H_xMe_yAl_zP_kO_2$; wherein, y+z+k=1 x is less than or equal to y;

y has a value ranging from 0.0008 to 0.4;

z has a value ranging from 0.25 to 0.67;

k has a value ranging from 0.2 to 0.67; and said molecular sieve having predominantly a plate crystal morphology having a width (W) and a thickness (T) wherein W/T is greater than or equal to 10, wherein the process of preparing the MeAPO molecular sieve includes the use of a texture influencing agent.

16. The process of claim 15, wherein the oxygenate feedstock comprises methanol, dimethyl ether, or a mixture thereof.

17. The process of claim 15, wherein the oxygenate feedstock comprises an organic sulphur feedstock.

18. The process of claim 15, wherein the oxygenate feedstock comprises an organic halide feedstock.

19. The process of claim 15, wherein the olefin products are fractionated to form a first stream comprising essentially ethylene and at least a part of said first stream is recycled for contact with the catalyst.

20. The process of claim 15, wherein the olefin products comprise ethylene that is further polymerized.

21. The process of claim 20, wherein the ethylene is further polymerized with one or more comonomers.

22. The process of claim 15, wherein the olefin products comprise propylene that is further polymerized.

23. The process of claim 22, wherein the propylene is further polymerized with one or more comonomers.

* * * * *